United States Patent [19]
Brown et al.

[11] Patent Number: 5,872,152
[45] Date of Patent: Feb. 16, 1999

[54] USE OF MMP INHIBITORS

[75] Inventors: Peter Duncan Brown; Lindsay Jayne Bawden; Karen Margrete Miller, all of Oxford, Great Britain

[73] Assignee: British Biotech Pharmaceuticals Limited, Cowley, United Kingdom

[21] Appl. No.: 686,485

[22] Filed: Jul. 26, 1996

Related U.S. Application Data

[63] Continuation of Ser. No. 133,081, filed as PCT/GB93/00888 Apr. 29, 1993, abandoned.

[30] Foreign Application Priority Data

May 1, 1992 [GB] United Kingdom .................. 9209513
Mar. 20, 1993 [GB] United Kingdom .................. 9305817

[51] Int. Cl.[6] .................................................. A01N 37/28
[52] U.S. Cl. ........................................................ 514/575
[58] Field of Search ............................................ 514/575

[56] References Cited

U.S. PATENT DOCUMENTS 5,256,657  10/1993  Singh et al. ......................... 514/228.2

FOREIGN PATENT DOCUMENTS

| 236872 | 9/1987 | European Pat. Off. . |
|---|---|---|
| 273689 | 6/1988 | European Pat. Off. . |
| 0320118 | 6/1989 | European Pat. Off. . |
| 320118 | 6/1989 | European Pat. Off. . |
| 322184 | 6/1989 | European Pat. Off. . |
| 401963 | 12/1990 | European Pat. Off. . |
| 0424193 | 4/1991 | European Pat. Off. . |
| 9010228 | 9/1990 | WIPO . |
| 0911193 | 8/1991 | WIPO . |

OTHER PUBLICATIONS

Liotta et al., "Cancer Metastasis and Angiogenesis: An Imbalance of Positive and Negative Regulation," Cell, 84:327–336 (1991).

Tamargo et al., "Angiogenesis Inhibitation by Minocycline," Cancer Research, 51:672–675 (1991).

Faucher, et al., "An Inhibitor of Mammalian Collagenase . . . Actinomycete Culture Broth," J. Antibiotics, vol. XI, No. 12, pp. 1757–1761 (1987).

*Primary Examiner*—Paul J. Killos
*Attorney, Agent, or Firm*—Hale and Dorr LLP

[57] ABSTRACT

Various known compounds which are matrix metalloprotease inhibitors have been found to be useful in the preparation of agents for promoting tumour regression and/or inhibiting cancer cell proliferation.

5 Claims, 2 Drawing Sheets

USE OF MMP INHIBITORS

This application is a continuation of application Ser. No. 08/133,081, filed Dec. 2, 1993, now abandoned, which is a 371 of PCT/GB93/00888 filed Apr. 29, 1993.

This application relates to the novel use of matrix metalloprotease (MMP) inhibitors for inhibition of angiogenesis and inhibition of cancer cell proliferation. This causes, inter alia, regression of tumours and is useful in the treatment of cancer.

Growth of tumours occurs both by local/regional spread and by a process of dissemination from the primary lesion known as metastasis, which gives rise to multiple secondary lesions that render the cancer unresectable. Patients with inoperable cancer include those with primary lesions with poorly defined margins and those with widespread metastatic disease. These patients cannot be cured by the currently available therapies. Such patients include those with breast, lung or colorectal carcinoma, and, for them, the prognosis remains poor (pain, decline in performance status and ultimately death), due to the inability to treat effectively disseminated forms of these cancers.

A major problem with the prior art is that most methods of treatment which are designed to kill disseminated cancer cells are highly toxic to normal (non-cancer) cells and can therefore only be administered for limited periods of time. A very desirable goal in cancer treatment is therefore to be able to produce necrosis of the tumour cells without toxic side effects, and thus prolong survival of the patient.

It has now surprisingly been discovered that various matrix metalloprotease inhibitors, such as inhibitors of collagenases, stromelysins and gelatinases, may be effective in bringing about tumour regression. Many compounds are known which are active as matrix metalloprotease inhibitors and which are not believed to be cytotoxic and the use of such compounds may therefore provide a breakthrough in cancer therapy, and in the treatment of diseases where angiogenesis is important, such as diabetic retinopathy, pterygia, psoriasis and atherosclerosis.

Although it might be possible to use endogenous MMP inhibitors in this manner, there is a problem associated with their large size ($M_r$ 20–30 kD) which excludes them from microenvironments within the tumour and thus limits their practical use. Further, endogenous MMP inhibitors such as TIMP 2 may also act as cytokines (Docherty et al. , Nature 318 66–69 (1985), giving rise to non-specific side effects.

The present invention therefore concerns a method of management of cancer in mammals, in particular humans, the method comprising administering to the mammal an effective amount of a non-endogenous matrix metalloproteinase inhibitor or a pharmaceutically or veterinarily acceptable salt thereof.

Therefore, in a first aspect of the invention, there is provided the use of a non-endogenous matrix metalloproteinase inhibitor in the preparation of an agent for promoting tumour regression and/or promoting the formation of avascular tumours.

Matrix metalloproteases have been shown to play an important role in the cancer-mediated degradation of extracellular matrix. This matrix acts as a "host-defence" mechanism in xenograft models of cancer spread forming an impenetrable barrier (DeVore et al., Expl. Cell Biol. 48 367–373, 1980). Degradation enables the cancer cells to move through the extracellular matrix, and both to enter and exit the vasculature; these steps are integral to the process of metastasis, which may occur early or late in the growth of the primary tumour, depending on tumour type.

However, the present invention does not relate to metastasis per se but rather to the tumour growth process occurring either before or after the metastatic spread via vascular and lymphatic channels. This invention therefore extends considerably the known clinical utility of matrix metalloproteinase inhibitors by enabling the treatment of patients with established metastases or inoperable malignant disease. Such patients are currently incurable.

It has also been shown that the products of matrix degradation may stimulate cancer cell invasion directly (Turpeenniemi-Hujanen et al., J. Biol. Chem. 261 1883–1889, 1986). Inhibition of degradation of extracellular matrix by the native metalloprotease inhibitor TIMP-2 has also been shown to arrest cancer growth (DeClerk et al., Cancer Res. 52 701–708, 1992), and TIMP has been shown to inhibit tumour-induced angiogenesis in experimental systems (Moses et al., Science 1990 248 1408–1410).

Although it can be deduced from these documents that TIMP-2 may be useful in the treatment of cancer, it has never previously been shown that small non-endogenous MMP inhibitors may have anti-tumour effects. In addition, it is possible that TIMP-2 is acting as a cytokine rather than an inhibitor of MMP (Docherty et al. 1985).

However, the work of the present inventors has shown that MMP inhibitors do not simply retard tumour growth but that, in fact, they actually promote tumour regression. This is a most surprising finding since it has never before been suggested that treatment of a tumour with these compounds may actually cause a tumour to decrease in size. It is therefore possible that in some cases cancer could be cured simply by the administration of MMP inhibitors.

Furthermore, it has now also been shown that any tumours which do develop in patients treated with MMP inhibitors are likely to be of significantly reduced size and avascular. Tumours lacking a Vasculature do not appear to grow beyond a size of a few mm$^3$ and do not represent a threat to patient health (Gimbrone et al, J. Exp. Med. 136, 261–276 (1972) ; Macchiarini et al., Lancet, 340 145–46 (1992); Weidener et al., N. Engl. J. Med. 324 1–8 (1991)).

In addition to tumour regression and promotion of avascular tumour formation, it has also been found that MMP inhibitors have other useful effects on tumour growth and therefore, in a second aspect of the invention there is provided the use of an MMP inhibitor in the preparation of an agent for inhibiting cancer cell proliferation.

It is preferred that MMP inhibitors are used in the treatment of tumours which cannot be cured by surgery. Tumours which often can be cured by surgery include, for example, single primary lesions with defined margins, benign tumours and some malignant tumours with solitary metastases. Examples of tumours which often cannot be cured by surgery are breast, ovarian, colorectal, neuroectodermal, lung, gastric, renal, pancreatic, cervical or prostate carcinomas, melanomas, sarcomas or ascites thereof.

MMP inhibitors may be used especially in the treatment of ovarian carcinomas, tumours of neuroectodermal origin or melanomas.

There are a vast number of compounds which are known to have MMP activity and some of these are described in EP-A-0320118, EP-A-0322184, EP-A-0358305, EP-A-0401963, EP-A-0214639, EP-A-0189784, EP-A-0126974, EP-A-0185380, EP-A-0159396, EP-A-0273689, EP-A-0236872, EP-A-0276436, U.S. Pat. No. 4,559,361 and U.S. Pat. No. 4,111,9951. In addition, our co-pending applications numbers WO-A-9005719, WO-A-9005716, WO-A-9102716 and International Patent Application No A-9102716 and International Patent Application No PCT/GB92/00230 also describe compounds which are useful as MMP inhibitors.

Any of these compounds can be used in the treatment of tumours but preferred compounds include those which contain a hydroxamic acid moiety. Examples of such compounds are those described in EP-A-0236872 which have the general formula:

wherein

A is HN (OH) CO or HCON (OH)

$R^1$ is $C_2$–$C_5$ alkyl $R^2$ is the characterising group of a natural α amino acid which may be protected provided that $R^2$ is not H or methyl;

$R^3$ is H, $NH_2$, OH, SH, $C_1$–$C_6$ alkyl, $C_1$–$C_6$ alkoxy, $C_1$–$C_6$ alkylamino, $C_1$–$C_6$ alkylthio or aryl ($C_1$–$C_6$ alkyl) group or amino-$C_1$–$C_6$ alkyl, hydroxy-$C_1$–$C_6$ alkyl, mercapto-$C_1$–$C_6$ alkyl or carboxy-$C_1$–$C_6$ alkyl where the amino, hydroxy, mercapto or carboxyl group can be protected, the amino group acylated or the carboxyl group amidated;

$R^4$ is H or methyl;

$R^5$ is H or $C_1$–$C_6$ alkyl, $C_1$–$C_6$ alkoxy-$C_1$–$C_6$ alkyl, di($C_1$–$C_6$ alkoxy) methyl, carboxy, $C_1$–$C_6$ alkylcarbonyl, $C_1$–$C_6$ alkoxycarbonyl, arylmethoxycarbonyl, $C_1$–$C_6$ alkylaminocarbonyl or arylaminocarbonyl; and $R^6$ is H or methyl; or $R^2$ and $R^4$ together form a group $(CH_2)_n$ where n is an integer from 4 to 11; or $R^4$ and $R^5$ together form a trimethyl group.

The compounds of EP-A-0214639 are also preferred. These compounds have the general formula:

wherein $R^1$ is $C_1$–$C_6$ alkyl;

$R^2$ is $C_1$–$C_6$ alkyl, benzyl, hydroxybenzyl, benzyloxybenzyl, ($C_1$–$C_6$ alkoxy) benzyl or benzyloxy ($C_1$–$C_6$ alkyl)

A is a ($CHR^3$—$CHR^4$) or ($CR^3$=$CR^4$) group;

$R^3$ is hydrogen, $C_1$–$C_6$ alkyl, phenyl or phenyl ($C_1$–$C_6$ alkyl); and

$R^4$ is H or $C_1$–$C_6$ alkyl, phenyl ($C_1$–$C_6$ alkyl), cycloalkyl or cycloalkyl ($C_1$–$C_6$ alkyl).

Further preferred compounds are those described in EP-A-320118 which have the general formula wherein $R^1$ is hydrogen or hydroxy, $R^2$ is hydrogen or alkyl, $R^3$ is $C_3$–$C_6$ alkyl, $R^4$ is hydrogen, alkyl, —$CH_2Z$ where Z is optionally substituted phenyl or heteroaryl, or $R^4$ is a group $C(HOR^8)R^9$ where $R^8$ is hydrogen, alkyl of $CH_2Ph$ where Ph is optionally substituted phenyl, and $R^9$ is hydrogen or alkyl; and $R^5$ is hydrogen or alkyl.

EP-A-0322184 discloses N-(2-alkyl-3-mercapto-1,5 dioxoalkyl)glycinamide derivatives of general formula where $R^1$ is hydrogen, alkyl or optionally substituted aryl, $R^2$ is hydrogen or acyl such as CO alkyl or COZ where Z is optionally substituted aryl; $R^3$ is $C_{3-6}$ alkyl, $R^4$ is hydrogen, alkyl, —$CH_2R^{10}$ where $R^{10}$ is optionally substituted phenyl or heteroaryl, or $R^4$ is a group $C(HOR^{11})R^{12}$ where $R^{11}$ is hydrogen, alkyl or $CH_2Ph$ where Ph is optionally substituted phenyl, and $R^{12}$ is hydrogen or alkyl; and $R^5$ is hydrogen, alkyl or a group $C(HR^{13})COR^{14}$ where $R^{13}$ is hydrogen, or alkyl, and $R^{14}$ is hydroxy, alkoxy, or —$NR^6R^7$, where each of $R^6$ or $R^7$ is hydrogen or alkyl, or $R^6$ and $R^7$ together with the nitrogen atom to which they are bonded form a 5-, 6 or 7 membered ring with optional oxygen or sulphur atom in the ring or an optional further nitrogen atom optionally substituted by alkyl.

EP-A-358305 discloses mercapto-phenylalcanoylamino amides of general formula where $R^1$ and $R^2$ are independently hydrogen, alkyl, alkoxy, halogen or $CF_3$, $R^3$ is hydrogen, acyl, such as COalkyl, or COZ, where Z is optionally substituted aryl, or a group RS where R is an organic residue such that the group RS provides an in vivo cleavable disulphide bond; $R^4$ is $C_{3-6}$ alkyl, $R^5$ is hydrogen, alkyl, —$CH_2R^{10}$ where $R^{10}$ is optionally substituted phenyl or heteroaryl, or a group $C(HOR^{11})R^{12}$ where $R^{11}$ is hydrogen, alkyl or $CH_2Ph$ where Ph is optionally substituted phenyl, and $R^{12}$ is hydrogen or alkyl; and $R^6$ is hydrogen, alkyl or a group $C(HR^{13})COR^{14}$ where $R^{13}$ is hydrogen, or alkyl, and $R^{14}$ is hydroxy, alkoxy, or —$NR^7R^8$, where each of $R^7$ or $R^8$ is hydrogen or alkyl, or $R^7$ and $R^8$ together with the nitrogen atom to which they are bonded form a 5-, 6 or 7 membered ring with optional oxygen, sulphur or optionally substituted nitrogen atom in the ring; or $R^5$ and $R^6$ are joined together as $(CH_2)_m$ where m is an integer from 4 to 12; X is $(CH_2)_n$ where n is 0, 1, or 2; and Y is $CH_2$.

EP-A-0401963 discloses phosphonopeptides of general formula where R is hydrogen, $C_1$–$C_6$ alkyl or optionally substituted benzyl, R1 is hydrogen or C1-6 alkyl, R2 is C3-6 alkyl, $R^3$ is hydrogen, alkyl, —$CH_2Z$ where Z is optionally substituted phenyl or heteroaryl, or $R^3$ is a group $C(HOR^7)R^8$ where $R^7$ is hydrogen, alkyl or $CH_2Ph$ where Ph is optionally substituted phenyl, and $R^8$ is hydrogen or alkyl; and $R^4$ is —$CH_2$—$(CH_2)_n OR^5$, —$CH_2$—$(CH_2)_n OCOR^6$ or —$CH(R^9)COR^{10}$, where n is an integer from 1 to 6; $R^5$, $R^6$ and $R^9$ are hydrogen or $C_1$–$C_6$ alkyl; and R10 is hydroxy or $OC_1$–$C_6$ alkyl or $NR^5R^6$ where $R^5$ and $R^6$ may be linked to form a heterocyclic ring; or $R^3$ and $R^4$ are joined together as $(CH_2)_m$ where m is an integer from 4 to 12.

Particularly preferred compounds for the use of the invention are those described in our co-pending applications mentioned above. WO-A-9005719 describes compounds of general formula $R^1$ represents a hydrogen atom $C_1$–$C_6$ alkyl, phenyl, thienyl, substituted phenyl, phenyl($C_1$–$C_6$)alkyl, heterocyclyl, ($C_1$–$C_6$)alkylcarbonyl, phenacyl or substituted phenacyl group; or, when n=0, $R^1$ represents $SR^x$, wherein $R^x$ represents a group:

$R^2$ represents a hydrogen atom or a $C_1$–$C_6$ alkyl, $C_1$–$C_6$ alkenyl, phenyl($C_1$–$C_6$)alkyl, cycloalkyl ($C_1$–$C_6$)alkyl or cycloalkenyl($C_1$–$C_6$)alkyl group;

$R^3$ represents an amino acid side chain or a $C_1$–$C_6$ alkyl, benzyl, ($C_1$–$C_6$ alkoxy)benzyl, benzyloxy($C_1$–$C_6$ alkyl) or benzyloxybenzyl group;

$R^4$ represents a hydrogen atom or a $C_1$–$C_6$ alkyl group;

$R^5$ represents a hydrogen atom or a methyl group;

n is an integer having the value 0, 1 or 2; and

A represents a $C_1$–$C_6$ hydrocarbon chain, optionaly substituted with one or more $C_1$–$C_6$ alkyl, phenyl or substituted phenyl groups;

and their salts and N-oxides.

Secondly WO-A-9005716 discloses hydroxamic acid based MMP inhibitors of general formula wherein $R^1$ is H, $C_1$–$C_6$ alkyl, $C_2$–$C_6$ alkenyl, phenyl, phenyl ($C_1$–$C_6$)alkyl, $C_1C_6$ alkylthiomethyl, phenylthiomethyl, substituted phenylthiomethyl, phenyl($C_1$–$C_6$ alkylthiomethyl, or heterocyclylthiomethyl or R1 represents —SRx wherein Rx represents a group $R^2$ represents a hydrogen atom or a $C_1$–$C_6$ alkyl, $C_1$–$C_6$ alkenyl, phenyl($C_1$–$C_6$)alkyl, cycloalkyl($C_1$–$C_6$)alkyl, or cycloalkenyl ($C_1$–$C_6$) alkyl;

$R^3$ represents an amino acid side chain or a $C_1$–$C_6$ alkyl, benzyl, ($C_1$–$C_6$)alkoxybenzyl, benzyloxy($C_1$–$C_6$)alkyl or benzyloxybenzyl group;

$R^4$ represents a hydrogen atom or a methyl group;

n is an integer from 1 to 6; and

A represents the group —$NH_2$, a substituted acyclic amine or a heterocyclic base;

or a salt and/or N-oxide and/or (where the compound is a thio-compound) a sulphoxide or sulphone thereof.

WO-A-9102716 discloses hydroxamic acid based MMP inhibitors of general formula wherein $R^1$ represents a hydrogen atom or a $C_1$–$C_6$ alkyl, $C_1$–$C_6$ alkenyl, phenyl, phenyl($C_1$–$C_6$)alkyl, $C_1$–$C_6$ alkylthiomethyl, phenylthiomethyl, substituted phenylthiomethyl, phenyl($C_1$–$C_6$)alkylthiomethyl or heterocyclylthiomethyl group; or $R^1$ represents —S—$R^x$, wherein $R^x$ represents a group

$R^2$ represents a hydrogen atom or a $C_1$–$C_6$ alkyl, $C_1$–$C_6$ alkenyl, phenyl($C_1$–$C_6$)alkyl, cycloalkyl($C_1$–$C_6$)alkyl, or cycloalkenyl($C_1$–$C_6$)alkyl;

$R^3$ represents an amino acid side chain or a $C_1$–$C_6$ alkyl, benzyl, ($C_1$–$C_6$) alkoxybenzyl, benzyloxy($C_1$–$C_6$)alkyl or benzyloxybenzyl group;

$R^4$ represents a hydrogen atom or a methyl group;

$R^5$ represents a group $(CH_2)_nA$;

or $R^4$ and $R^5$ together represent a group wherein

Q represents $CH_2$ or CO;

m is an integer from 1 to 3; and n is an integer from 1 to 6; and

A represents a hydroxy, $(C_1-C_6)$alkoxy, $(C_2-C_7)$acyloxy, $(C_1-C_6)$alkylthio, phenylthio, $(C_2-C_7)$acylamino or N-pyrrolidone group
or a salt and/or N-oxide and/or (where the compound is a thio-compound) a sulphoxide or sulphone thereof.

PCT/GB92/00230 discloses compounds of general formula wherein
$R^1$ is hydrogen, $C_1-C_6$ alkyl, phenyl, substituted phenyl, phenyl($C_1-C_6$ alkyl), or heterocyclyl; or
$R^1$ is $ASO_nR^7$; wherein
A represents a $C_1-C_6$ hydrocarbon chain, optionally substituted with one or more $C_1-C_6$ alkyl, phenyl or substituted phenyl groups
n=0, 1, 2;
$R^7$ is $C_1-C_6$ alkyl, phenyl, substituted phenyl, phenyl ($C_1-C_6$ alkyl), heterocyclyl, ($C_1-C_6$ alkyl)acyl, thienyl or phenacyl;
$R^2$ is hydrogen, $C_1-C_6$ alkyl, $C_2-C_6$ alkenyl, phenyl ($C_1-C_6$alkyl) or cycloalkyl ($C_1-C_6$ alkyl);
$R^3$ and $R^4$ are selected from hydrogen, halogen, cyano amino, amino ($C_1-C_6$) alkyl, amino di($C_1-C_6$)alkyl, amino ($C_1-C_6$) alkylacyl, aminophenacyl, amino (substituted) phenacyl, amino acid or derivative thereof, hydroxy, oxy ($C_1-C_6$)alkyl, oxyacyl, formyl, carboxylic acid, carboxamide, carboxy($C_1-C_6$) alkylamide, carboxyphenylamide, carboxy($C_1-C_6$) alkyl, hydroxy ($C_1-C_6$)alkyl, ($C_1-C_6$)alkyloxy($C_1-C_6$) alkyl or acyloxy ($C_1-C_6$)alkyl, ($C_1-C_6$)alkylcarboxylic acid, or ($C_1-C_6$) alkylcarboxy($C_1-C_6$) alkyl;
or $R^3$ is $OCH_2COR^8$ and $R^4$ is hydrogen;
wherein
$R^8$ is hydroxyl, $C_1-C_6$ oxyalkyl, $C_1-C_6$ oxyalkylphenyl, amino, $C_1-C_6$ aminoalkyl, $C_1-C_6$ aminodialkyl, $C_1-C_6$ aminoalkylphenyl, an amino acid or derivative thereof;
or $R^3$ is $OCH_2CH_2OR^9$ and $R^4$ is hydrogen;
wherein
$R^9$ is $C_1-C_6$ alkyl, $C_1-C_6$ alkylphenyl, phenyl, substituted phenyl, ($C_1-C_6$ alkyl)acyl, or phenacyl;
or $R^3$ is $OCH_2CN$ and $R^4$ is hydrogen;
$R^5$ is hydrogen or $C_1-C_6$ alkyl, or ($C_1-C_6$) alkylphenyl;
$R^6$ is hydrogen or methyl;
or a salt thereof.

All of these compounds are said to be useful in the management of diseases such as arthritis, but there is no suggestion that they could be used to promote tumour regression.

As used herein the term "$C_1-C_6$ alkyl" refers to straight chain or branched chain hydrocarbon groups having from one to six carbon atoms. Illustrative of such alkyl groups are methyl, ethyl, propyl, isopropyl, butyl, isobutyl, sec-butyl, tert-butyl, pentyl, neopentyl and hexyl.

As used herein the term "$C_2-C_6$ alkenyl" refers to straight chain or branched chain hydrocarbon groups having from two to six carbon atoms and having in addition one or more double bonds, each of either E or Z stereochemistry where applicable. This term would include for example, vinyl, 1-propenyl, 1- and 2-butenyl and 2-methyl-2-propenyl.

As used herein, the term "$C_3-C_6$ cycloalkyl" refers to an alicyclic group having from 3 to 6 carbon atoms. Illustrative of such cycloalkyl groups are cyclopropyl, cyclobutyl, cyclopentyl and cyclohexyl.

As used herein, the term "$C_4-C_6$ cycloalkenyl" refers to an alicyclic group having from 4 to 6 carbon atoms and having in addition one or more double bonds. Illustrative of such cycloalkenyl groups are cyclopentenyl, cyclohexenyl, cycloheptenyl and cyclooctenyl.

As used herein, the term "halogen" refers to fluorine, chlorine, bromine or iodine.

As used herein, the term "amino acid side chain" refers to a characteristic side chain attached to the $—CH(NH_2)$ (COOH) moiety in the following R or S amino acids: glycine, alanine, valine, leucine, isoleucine, phenylalanine, tyrosine, tryptophan, serine, threonine, cystein, methionine, asparagine, glutamine, lysine, histidine, arginine, glutamic acid and aspartic acid.

Particularly preferred compounds for use in the treatment of tumours are

1 [4-(N-hydroxyamino)-2R-isobutyl-3S-thienylthiomethyl) succinyl]-L-phenylalanine-N-methylamide (compound I) of which the formula is given below 2 [4-(N-hydroxyamino)-2R-isobutyl-3S-phenylthiomethyl) succinyl]-L-phenylalanine-N-methylamide (compound II) of which the formula is given below MMP inhibitors may be prepared for administration by any route. The compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrollidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practise. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The dosage unit involved in oral administration may contain from about 1 to 250 mg, preferably from about 25 to 250 mg of a compound of general formula I. A suitable daily dose for a mammal may vary widely depending on the condition of the patient. However, a dose of a compound of general formula I of about 0.1 to 300 mg/kg body weight, particularly from about 1 to 100 mg/kg body weight may be appropriate.

The following examples illustrate the invention, but are not intended to limit the scope in any way.

EXAMPLE 1
Inhibition of Cell Proliferation.

A pronounced cytostatic effect of Compound I was observed microscopically when this compound was added to RPMI-7951 human melanoma cells (available from ATCC) at a concentration of 3 $\mu$M. To quantify these observations, the effect of Compound I on DNA synthesis was examined using a thymidine incorporation assay.

RPMI-7951 cells were seeded onto 24-well tissue culture plates at a density of $1 \times 10^4$/well in Dulbecco's Modified Eagle Medium containing 5% fetal bovine serum. Compound I was dissolved in absolute ethanol to provide a range of 500× stocks which gave final concentrations in the assay of between 6 $\mu$M and 30 nM. The final concentration of ethanol in each well was 0.2%. Compound I was added directly to wells, 4 hours after seeding and again 24 hrs after seeding. $^3$H-thymidine (1 $\mu$Ci/well) was added to each well 46 hrs after seeding for a period of 2 hours. After this period the medium was removed and 1 ml of ice-cold 5% (w/v) trichloroacetic acid (TCA) added to each well. The plates were left on ice for 30 min and then washed three times with 5% (w/v) TCA (1 ml/well) and twice with absolute ethanol (1 ml/well). After drying, the TCA-insoluble material was solubilised in 0.25% (w/v) trypsin (300 $\mu$l/well) for 1 hour followed by the addition of 1% (w/v) sodium dodecyl sulphate (300 $\mu$l/well). An aliquot (500 $\mu$l) was taken for scintillation counting. The assay was performed in duplicate and the incorporated $^3$H-thymidine in each well was expressed as a percentage of the mean value from duplicate wells in which the cells received ethanol vehicle only. The results of the experiment are shown in Table 1.

TABLE 1

| Concentration Compound I (nM) | Incorporated DPM | % Ethanol Control | % Inhibition |
|---|---|---|---|
| 6000 | 4154 ± 113 | 43.0 | 57.0 |
| 3000 | 4813 ± 44 | 49.6 | 50.4 |
| 1000 | 5798 ± 297 | 59.7 | 40.3 |
| 300 | 7168 ± 111 | 73.8 | 26.2 |
| 100 | 7682 ± 27 | 79.1 | 20.9 |
| 30 | 8825 ± 2 | 90.9 | 9.1 |
| Ethanol | 9702 ± 238 | | |
| No Addition | 10346 ± 354 | 106 | |

Compound II was also tested for cytostatic activity in the erythroleukaemic line K562 and the neuroblastoma cell line IRM 32 (both available from ATCC) were plated into 96 well plates at a density of 5,000 cells/well in RPMI 1640 medium with 10% foetal calf serum. Compound II was added to duplicate wells in the same medium giving a final volume of 200 $\mu$l per well. Appropriate control cultures were also set up. The plates were incubated for 96 hours and then the number of cells per well were determined using a Promega Celltitre colourimetric assay with a standard curve generated using known numbers of cells per well. The assay is based on the uptake and conversion to formazan of the tetrazolium salt 3-(4,5 dimethylthiazol-2-yl)-2,5,-diphenyl tetrazolium bromide. Cell proliferation in the presence of Compound II was expressed as a percentage of the growth of control, untreated cultures and is shown in Table 2.

TABLE 2

| Concentration of Compound II ($\mu$M) | % Control | | proliferation | |
|---|---|---|---|---|
| | IRM32 | (SD) | K562 | (SD) |
| 100 | 17.44 | (2.25) | 20.81 | (0.39) |
| 50 | 23.95 | (0.24) | 25.42 | (0.69) |
| 25 | 29.80 | (2.70) | 31.11 | (4.90) |
| 12.5 | 38.29 | (4.40) | 30.10 | (2.90) |
| 6.25 | 35.18 | (0.62) | 34.45 | (0.91) |
| 3.125 | 49.63 | (10.9) | 36.25 | (2.68) |
| 1.562 | 42,58 | (9.76) | 45.09 | (1.43) |
| 0.781 | 57.97 | (10.35) | 52.86 | (7.14) |
| 0.391 | 74.52 | (0.66) | 67.57 | (1.13) |
| 0.195 | 93.46 | (1.07) | 77.36 | (11.33) |
| 0.095 | n/d | | 89.91 | (17.17) |
| 0.488 | n/d | | | |
| | 90.46 | (1.82) | | | n/d - not determined

As is clear from the above Tables, Compounds I and II have cytostatic activity. Although this cytostatic activity may be mediated by MMP inhibition, it is also possible that Compound I could act directly on DNA synthesis as previous studies have demonstrated hydroxamate-mediated inhibition of DNA synthesis (Gale, *Experientia*, 24, 57–58, 1968). However, much higher concentrations ($IC_{50}$ 400-50 $\mu$M) were required than the concentrations shown to be effective in the present invention.

In order to determine whether Compound 1 affects DNA synthesis in cells, human ovarian cells are seeded onto 24-well tissue culture plates at a density of $1 \times 10^4$/well in RPMI-1640 medium containing 5% fetal bovine serum. Compound I is dissolved in absolute ethanol to provide a range of 500× stocks with final concentrations in the assay of between 6 $\mu$M and 30 nM. The final concentration of ethanol in each well is 0.2%. Compound I is added directly to wells, 4 hours after seeding and again 24 hrs after seeding. $^3$H-Thymidine (1 $\mu$Ci/well) is added to each well 46 hrs after seeding for a period of 2 hours. After this period the medium is removed and 1 ml of ice-cold 5% (w/v) trichloroacetic acid (TCA) added to each well. The plates are left on ice for 30 min and then washed three times with 5% (w/v) TCA (1 ml/well) and two times with absolute ethanol (1 ml/well). After drying, the TCA-insoluble material is solubilised in 0.25% (w/v) trypsin (300 µl/well) for 1 hour followed by the addition of 1% (w/v) sodium dodecyl sulphate (300 µl/well). An aliquot (500 µl) is taken for scintillation counting.

EXAMPLE 2

Use of Animal Cancer Models to Demonstrate Tumour Regression and Inhibition of Tumour Growth by Hydroxamic Acids Subcutaneous Tumour Growth Inhibition of Subcutaneous B16-BL6 Tumour growth B16-BL6 melanoma cells were injected subcutaneously into the flanks of C57/BL6/J mice (200,000 cells/site, one site per animal). Compound I was administered as a suspension (2.5 mg/ml) in phosphate-buffered saline containing 0.01% Tween80 at 30 mg/kg, i.p., u.i.d. from day 1 to day 19 or day 11 to day 19. Vehicle alone was admininstered to the control group according to the same schedule. Tumour weight was calculated according to the following formula:

Weight=length×width$^2$/2.

Figure 1:
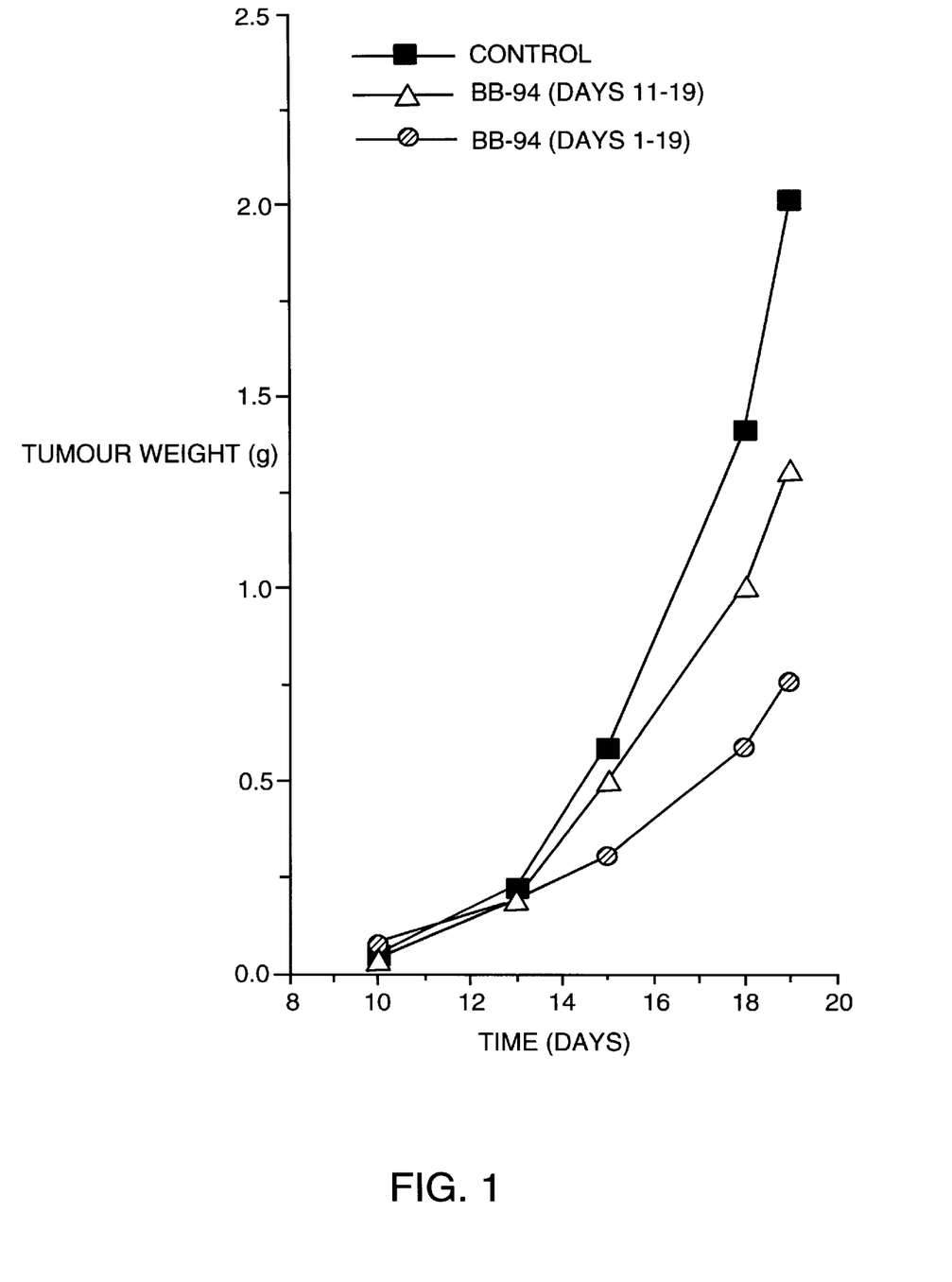
FIG. 1 shows the inhibition of subcutaneous B16 melanoma tumor growth by compound I, BB-94.

Each data point represents the median value from six animals. Administration of Compound I reduced the tumour burden of the animals. The results are shown in FIG. 1.

Six to eight week old female or male nude mice are injected subcutaneously with 1×10$^4$ to 1×10$^6$ human tumour cells, in particular A2058 and RPMI-7951 melanoma cells, MDA-MB-231, MDA-MB-436, DU4475, and H$_S$ 578T breast carcinoma cells, and NCI-H69 and NCI-H128 lung carcinoma cells. Compound I is administered by the intraperitoneal, oral, intramuscular, or intravenous routes once to three times per day, for a period of 1 to 30 days following tumour cell administration. For the purpose of demonstrating tumour regression, Compound I is administered for a period of 1 to 20 days commencing 7–10 days after tumour cell administration. Subcutaneous tumour growth is monitored by daily measurement of tumour diameter by caliper. Final tumour burden is determined by complete excision and weighing. The extent of tumour necrosis is determined by microscopic histological examination. The effect of Compound I is assessed relative to a control group of nude mice that receive tumour cells and the Compound I vehicle only.

Intraperitoneal Tumour Growth

Six to eight week old female or male nude mice are injected intraperitoneally with 1×10$^4$ to 5×10$^6$ human tumour cells, in particular gastric or ovarian carcinoma cells. Compound I is administered by the intraperitoneal, oral, intramuscular, or intravenous routes once to three times per day, for a period of 1 to 30 days following tumour cell administration. For the purpose of demonstrating tumour regression, Compound I is administered for a period of 1 to 20 days commencing 7–10 days after tumour cell administration. Final tumour burden is determined by complete excision and weighing. The extent of tumour necrosis is determined by microscopic histological examination. The effect of Compound I is assessed relative to a control group of nude mice that received tumour cells and the Compound I vehicle only.

Lung Colony Tumour Growth

Inhibition of Lung Tumour growth

AP5 is a human colorectal carcinoma line which grows as colonies within the lungs of SCID mice following iv administration.

Mice received a single iv injection of 4×10$^4$ AP5 cells in a 200 µl volume of PBS. Compound I was administered ip once per day, for a period of 28 days. Mice were observed daily and weighed twice weekly. At termination, lungs were dissected, nodules counted and the lungs weighed. The lungs of 5 non-tumour-bearing SCIDs were also weighed to determine the mean tumour-free lung weight. The results are shown in Table 3.

TABLE 3

| Treatment | Dose | Median wt metastases (g) | SEM | p-value (Mann-Whitney) |
|---|---|---|---|---|
| Vehicle | Days 1–25 u. i .d | 0.18 | 0.02 | |
| Compund I | Days 1–25 u. i. d | 0.13 | 0.05 | <0.05 |

Six to eight week old female or male nude mice are injected intravenously with 1×10$^4$ to 1×10$^5$ human tumour cells, in particular A2058 and RPMI-7951 melanoma cells, and NCI-H69 and NCI-H128 lung carcinoma cells. Compound I is administered by the intraperitoneal, oral, intramuscular, or intravenous routes once to three times per day, for a period of 1 to 30 days following tumour cell administration. For the purpose of demonstrating tumour regression Compound I is administered for a period of 1 to 20 days commencing 7–10 days after tumour cell administration. Final tumour burden is determined by counting the number of lung colonies and by image analysis of colony size. The extent of tumour necrosis is determined by microscopic histological examination. The effect of Compound I is assessed relative to a control group of nude mice that received tumour cells and the Compound I vehicle only.

EXAMPLE 3

Inhibition of angiogenesis

In vitro

The potential of native tissue inhibitor of metalloproteinase-1 (TIMP-1) to inhibit the process of blood vessel formation, or angiogenesis, has been demonstrated in a variety of experimental systems. The purpose of the current study was to investigate whether Compound I, a low molecular weight synthetic inhibitor of matrix metalloproteinases, could inhibit the formation and development of blood vessels in an in vitro system. The system chosen was that described by Nicosia and Ottinetti in which vessel growth is measured from fragments of rat aorta cultured in fibrin or collagen gels (Nicosia, R F and Ottinetti, A. Lab Invest 63 115–122 (1990)).

A sterile solution of 1.5% (w/v) agarose was poured into 100×15 mm culture dishes and allowed to gel. Agarose rings (int. diam. 10 mm, ext. diam. 17 mm) were cut with sterilised nylon ring punches and were transferred to 6 well dishes (1 ring per well, 3 wells per experimental condition). Thoracic aortas were dissected from 12 week-old male Wistar rats and rapidly transferred to a culture dish containing serum-free preservation medium (Hanks balanced salt solution containing 1% HSA, 100 U/ml penicillin, 100 µg/ml streptomycin, 0.25 µg/ml fungizone). Fibroadipose tissue was removed under a dissecting microscope, and 1 mm long aortic rings were sectioned. Prior to embedding the aortic rings, the bottom of the agarose wells were coated with 100 µl of fibinogen gel solution (3 mg/ml rat fibrinogen in serum-free culture medium containing 0.2 NIH units/ml human thrombin and 6.9 mM CaCl$_2$). After the fibrin gel had formed, an aortic ring was deposited in the centre and a second layer of fibrinogen gel solution was poured on top. Compound I or dimethylsulphoxide (DMSO) vehicle was added to the dish with serum-free culture medium (DMEM/F12 1:1, 10 mM $MgCl_2$, 300 μg/ml ε-aminocaproic acid, 100 U/ml penicillin, 100 μg/ml streptomycin, and 25 μg/ml fungizone) on days 0, 2, 4, and 6. The microvessels were counted on a daily basis; the number for each experimental condition was expressed as the mean of three wells.

Compound I inhibited both the rate of development and the total number of microvessels in two separate experiments. Compound I was active in the model at all concentrations tested (2–0.05 μM). DMSO at a concentration of 0.1% (v/v) had no effect on the number of microvessels. This result demonstrates the anti-angiogenic potential of Compound I.

In vivo

The process of new blood vessel formation, or angiogenesis, can be studied using subcutaneously implanted polyester sponges. These become filled with vascularised granulation tissue over a period of 2–3 weeks. This increase in vascularisation can be followed by monitoring the rate at which radioactive xenon ($^{133}Xe$) is cleared from the sponge.

Sterile discs of polyester sponge (1.2 cm diameter) with centrally placed polyethylene cannulas (1.4 mm internal diameter) were implanted in the backs of male Wistar rats. The discs were placed subcutaneously at a site 1–2 cm distant from the point of incision, and the cannulas pushed through a small opening in the skin. The cannulas were then plugged to prevent overt infection. Blood flow measurements were made in a temperature controlled room (20°±1° C.) with the animals treated with Hypnorm to induce neuroleptanalgesia. Xenon ($^{133}Xe$) was diluted in sterile physiological saline and injected in a final volume of 10 μl. The cannula was plugged to prevent evaporation and the clearance of $^{133}Xe$ monitored over a period of 6 minutes using a sodium iodide thallium activated crystal detector, positioned 1 cm over the sponge cannula. The radioactivity was recorded every 40 seconds and printed automatically on an SR7 scaler ratemeter. The clearance of $^{133}Xe$ is given as the radioactivity detected at 6 minutes expressed as a percentage of the radioactivity at time zero. In untreated sponges the $^{133}Xe$ clearance is initially due to passive diffusion on day 1 but increases from day 6 until it reaches the clearance rate of normal skin by day 14.

Compound I, suspended in phosphate buffered saline containing 0.01% (v/v) Tween-80 (PBS-Tween), was administered in a total volume of 50 μl by direct injection into the sponge. Compound I was administered at doses of 300, 100, and 30 μg once daily following completion of the $^{33}Xe$ clearance measurement. Dexamethasone was administered by the same route at a dose of 5 μg u.i.d. PBS-Tween vehicle alone was administered to the control group. Each treatment group consisted of three sponges. The results are given as the mean ±s.e.m. The reduction in $^{133}Xe$ clearance in the dexamethasone group was found to be statistically significant on days 10, 12, and 14 (p<0.01) as measured by the two-tailed Student's t-test for unpaired data. The reduction in $^{133}Xe$ clearance in the group receiving 300 μg Compound I was found to be statistically significant on days 12 (p<0.05) and 14 (p<0.01), as was the reduction in the group receiving 100 μg Compound I (p<0.05).

EXAMPLE 4

Inhibition of malignant ascites

In this example, the cell line used was the HU human ovarian carcinoma cell line although, of course, other available ovarian carcinoma cell lines could also be used. Ovarian carcinoma spreads by direct extension into the peritoneum. The cancer cells implant on the serosal and visceral surfaces of the peritoneum and give rise to peritoneal ascites. The HU model of ovarian carcinoma exhibits both implanted and ascitic tumour growth. The HU cells are introduced directly into the peritoneum where they form ascites within 7 days. If tumour necrosis factor (TNF) is added at this point, the ascitic tumour cells implant and large solid tumours are formed by day 21. Compound I was tested for its ability to inhibit both forms of tumour growth.

HU ovarian carcinoma cells were passaged in vivo. Ascitic tumour was taken and diluted 1:1 with RPMI-1640 medium. Cells ($1\times10^6$/animal) were injected into the peritoneum on day 0 and the mice divided into 6 groups of 9. Compound I was administered by once daily intraperitoneal (i.p) injection as a suspension in phosphate buffered saline, pH7.2, (PBS) containing 0.01% (v/v) TWEEN-80 at 40 mg/kg from day 3 to day 20. (The expression TWEEN-80 is a trade mark.) Vehicle was administered to a control group over the same period. A solution of TNF in PBS containing 3 mg/ml bovine serum albumin was administered by once daily i.p injection at 1 μg/animal from day 7 to day 20. Vehicle (TNF diluent) was administered to a control group over the same period. The results are summarized in Table 4 below.

TABLE 4

| Group | Treatment | Day Killed | Result |
|---|---|---|---|
| 1 | TNF Diluent | 9 day 16* | Ascites (5–6 ml/animal) |
| 2 | Vehicle | 5 day 16* | Ascites (5–6 ml/animal) |
|   |   | 3 day 17* | Ascites (5–6 ml/animal) |
|   |   | 1 day 21 | No Tumour |
| 3 | Compound I | 9 day 21 | Small Solid Tumour |
| 4 | TNF | 9 day 21 | Large Solid Tumour |
| 5 | TNF + Vehicle | 9 day 21 | Large Solid Tumour |
| 6 | TNF + Compound I | 9 day 21 | Small Solid Tumour |

*Animals were only killed before day 21 if death was inevitable within a few hours. As such, this can be viewed as a survival endpoint and reflects the severity of ascites over the 21 day period.

The small tumours that formed in the Compound I treated animals of Groups 3 and 6 were avascular, as opposed to the vascularised solid tumours formed in the presence of TNF alone. Histological analysis revealed that these small tumours were composed principally of "host" stromal tissue with occasional islands of tumour cells exhibiting a glandular morphology. There were also large areas where these islands of tumour cells showed evidence of necrosis.

As discussed previously, these small avascular tumours, in contrast to the vascularised tumours, represent little threat to the patient.

Furthermore, the results of this example suggest that tumour regression is likely to occur in certain particular cases.

The effect of Compound I therapy on the survival of animals bearing the HU xenograft was investigated in a series of experiments in which the animals were killed when death from the malignancy was inevitable within a matter of hours. The results are summarised in Table 5.

Figure 2:
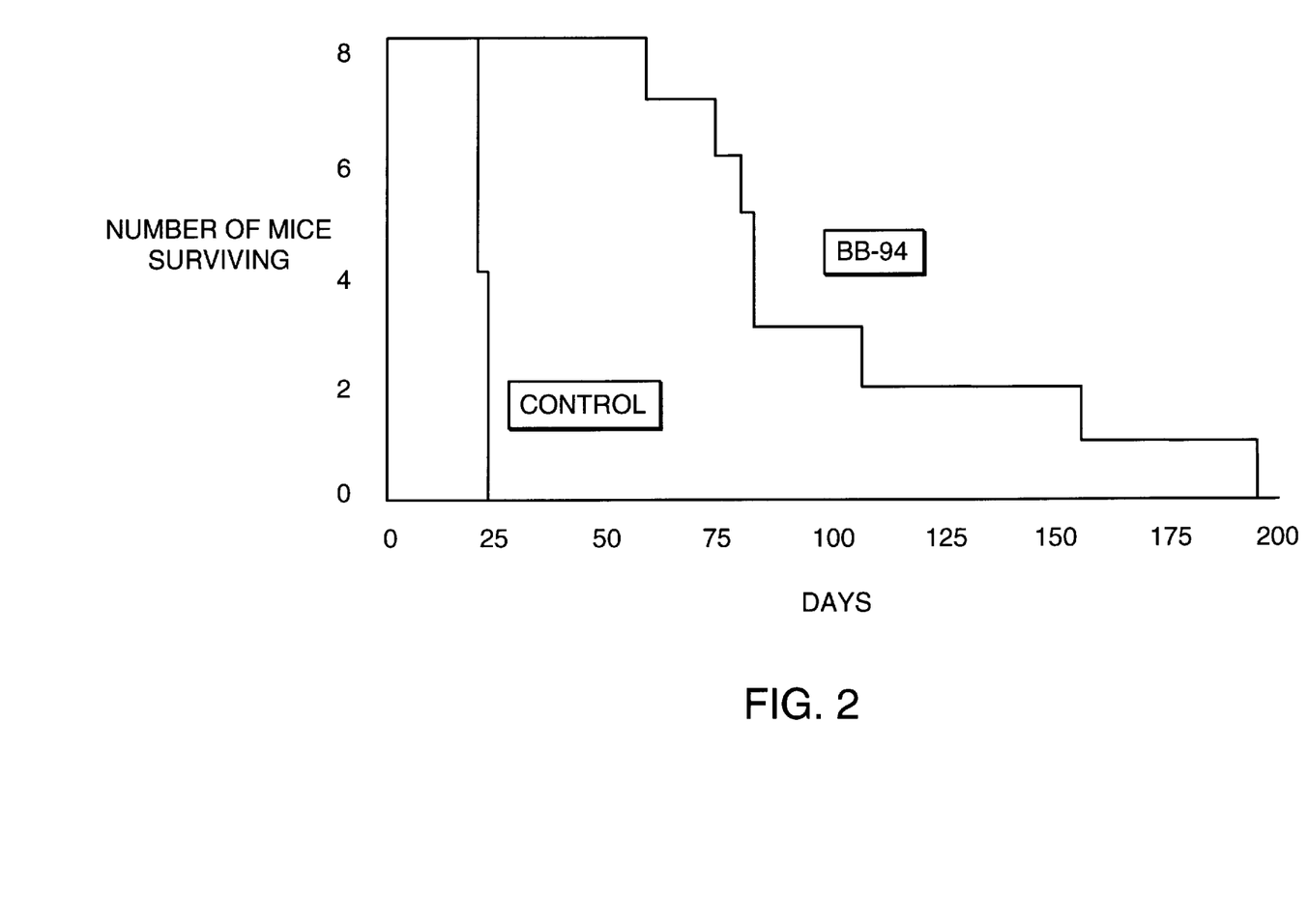
FIG. 2 shows the effect of compound I, (BB-94) treatment (days 7–20) on survival of mice in the HU ovarian carcinoma model.

Treatment of mice with Compound I at 40 mg/kg u.i.d. from days 3–20 and from days 7–20 resulted in increases in median survival times of 6.5 and 4.4 fold respectively. The latter result is of particular significance since the mice had 1–2 ml of established ascites at the time treatment commenced, indicating that Compound I therapy can resolve pre-existing malignant ascites. The results are summarised in FIG. 2. It is also clear from the subsequent studies that daily dosing with Compound I is likely to be unnecessary, and that even a single dose can confer a significant survival advantage.

TABLE 5

Effect of Compound I on the Survival of Mice bearing the HU Human Ovarian Carcinoma Xenograft

| Treatment of Schedule | | Number of Animals | Median Survival Time (days) (*p > 0.05) |
|---|---|---|---|
| Vehicle- | u. i. d. day 3–day 20 | 8 | 18.5 |
| Compound I- | 40 mg/kg u. i. d. day 3–day 20 | 8 | 120.0* |
| Vehicle- | u. i. d. day 7–day 20 | 8 | 18.5 |
| Compund I- | 40 mg/kg u. i. d. day 7–day 20 | 8 | 81.0* |
| Vehicle- | days 3, 6, 9, 15, 18 | 4 | 16.0 |
| Compound I- | 40 mg/kg days 3, 6, 9, 15, 18 | 4 | 147.0* |
| Compound I- | 40 mg/kg single dose on day 3 | 4 | 115.0* |
| Vehicle- | single dose on day 3 | 4 | 18.0 |
| Compound I- | 1 mg/kg single dose on day 3 | 4 | 18.0 |
| Compound I- | 10 mg/kg single dose on day 3 | 4 | 25.0 |
| Compound I- | 30 mg/kg single dose on day 3 | 4 | 32.0* |
| Compound I- | 40 mg/kg single dose on day 3 | 4 | 48.0* |

TABLE 6

Effect of Compound I in the LA Human Ovarian Carcinoma Model

| | Treatment | Days of Treatment | Result | |
|---|---|---|---|---|
| Group 1 | Diluent | 3–14 | 7 killed day 12 | Ascites (gel like consistency) |
| Group 2 | Compound I | 3–14 | 1 killed day 12 | Ascites, clear watery fluid with gelatinous tumours. 1 large tumour at base of spleen. |
| | | | 7 killed day 14 as planned | 5 had small solid tumours, 2 had 2 ml of red, clear acellular watery fluid. |

Compound I was also tested against a second ovarian carcinoma, the LA xenograft. Although the anti-tumour effect was not quite as strong with this xenograft, histological analysis of the small tumours in the treated animals revealed the mechanisms involved to be similar to those in the HU model. The tumours in the treated animals were avascular and were encapsulated with dense stromal tissue. The results are summarised in Table 6.

EXAMPLE 5

Clinical Administration of Compound I.

Patients are admitted to the ward. A peritoneal tap is inserted and malignant ascites drained. The volume of the appropriate dose of Compound I is calculated. It is added to a 500 ml bag of 5% dextrose less than 2 hours before administration and warmed to 37° C. To keep the outlets clear, the bag is inverted gently once or twice just before the infusion is commenced and again during the infusion.

The dose is given with the patient supine using a peritoneal dialysis catheter. The catheter is removed once dosing is complete.

We claim:

1. The method of promoting tumor regression in a patient comprising administering an effective amount of an exogenous matrix metalloprotease (MMP) inhibitor to said patient sufficient to promote tumor regression.

2. The method of claim 1, wherein said tumor is a solid tumor.

3. The method of claim 2, wherein said solid tumour is a breast, ovarian, neuroectodermal, lung, colorectal, gastric, renal, pancreatic, cervical or prostate carcinoma, a melanoma, a sarcoma, or an ascites thereof.

4. The method of inhibiting cancer cell proliferation in a patient comprising administering an effective amount of an exogenous matrix metalloprotease (MMP) inhibitor to said patient sufficient to inhibit cancer cell proliferation.

5. The method of any one of claims 1–3 and 4, wherein the MMP inhibitor contains a hydroxamic acid moiety or a protected version thereof.

* * * * *